United States Patent [19]

Kem

[11] Patent Number: 4,922,012

[45] Date of Patent: May 1, 1990

[54] COMPOSITIONS OF MATTER COMPRISING DIALKYL-(N,N-DIALKYLCARBAMOYL-METHYL) PHOSPHINE OXIDES

[75] Inventor: Kenneth M. Kem, San Juan Capistrano, Calif.

[73] Assignee: Occidental Chemical Corporation, Niagara Falls, N.Y.

[21] Appl. No.: 570,181

[22] Filed: Jan. 12, 1984

Related U.S. Application Data

[63] Continuation-in-part of Ser. No. 295,300, Aug. 24, 1987, abandoned, which is a continuation-in-part of Ser. No. 239,731, Mar. 2, 1981, Pat. No. 4,396,556.

[51] Int. Cl.$^5$ .............................. C07F 9/28; C07F 9/02
[52] U.S. Cl. .......................................... 564/15; 564/16; 423/9; 423/10
[58] Field of Search .................. 564/15, 16; 423/9, 10

[56] References Cited

U.S. PATENT DOCUMENTS 3,816,068  6/1974  Rivlin ...................................... 564/15
3,972,928  8/1976  Newallis et al. ....................... 564/15

OTHER PUBLICATIONS

Zabrusova et al., CA 66:10998h (1967).
Horwitz et al., Chem. Eng. News, p. 51 (7/13/81).

Primary Examiner—Carolyn S. Elmore
Attorney, Agent, or Firm—James F. Tao; Richard D. Fuerle

[57] ABSTRACT

Novel organic tertiary phosphine oxides for example, bidentate organophosphorus actinide extractants, such as the carbamoylmethylphosphine oxides (CMPO's) are disclosed, such compounds can be prepared (e.g., in 85% or better yield and purity) by a process involving phase transfer catalysis, under conditions where degradive hydrolysis of the products or reactants is substantially avoided. For example, tertiary carbamoylmethylphosphine oxides which are useful as extractants for transplutonium elements are disclosed and can be prepared by reaction of the corresponding secondary phosphine oxides with 2-substituted acetamides (wherever the substituent is a good leaving group, e.g., chlorine) in a two-phase system containing a high concentration of an aqueous base (preferably sodium hydroxide) and a suitable phase transfer catalyst, e.g., tetralkylammonium chlorides.

9 Claims, No Drawings

COMPOSITIONS OF MATTER COMPRISING DIALKYL-(N,N-DIALKYLCARBAMOYLMETHYL) PHOSPHINE OXIDES

This application is a continuation-in-part of U.S. patent application Ser. No. 295,300 filed Aug. 24, 1981 and now abandoned which is a continuation-in-part of Ser. No. 06/239,731, now U.S. Pat. No. 4,396,556.

BACKGROUND OF THE INVENTION

This invention involves certain novel dialkyl(N,N-dialkylcarbamoylmethyl) phosphine oxides which are useful as reagents for the fractionation of radionuclides (e.g., transplutonium elements) from nuclear process streams by solvent extraction (e.g., see U.S. Pat. No. 3,993,728 to Schultz) and/or for extracting uranium from wet process phosphoric acid (e.g., see U.S. Pat. No. 4,268,395 to Steward and U.S. Pat. No. 4,243,637 to Bradford and Ore). These novel phosphine oxides and others can be manufactured by the processes shown in copending application Ser. No. 239,731 filed Mar. 2, 1981, now U.S. Pat. No. 4,396,556, which is incorporated herein by reference. In general, these processes can make a phosphine oxide which can be represented by the general formula 1:

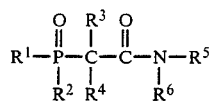

where R1, R2, R3, R4, R5 and R6 are alkyl, aryl or hydrogen.

The following general equations represent a preferred process for making certain novel compounds:

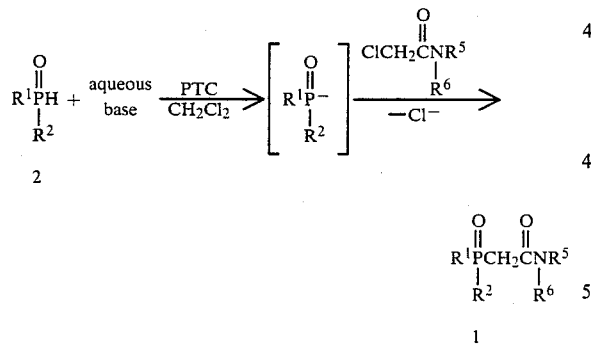

where PTC is a phase transfer catalyst.

In a preferred process, the alkylating reagent is stable in the presence of the base and the intermediate is converted rapidly to a desired product and not precipitated as a solid or converted to unwanted side products. Compounds of structure similar to those of this invention were, perhaps, implied by Siddall, *Aqueous Reprocess Chem. Irradiated Fuels Sym.*, 57 (1964), and Siddall and Davis, *J. Chem. Eng. Data*, 10(3), 303 (1965). In these papers, no example of how to prepare any such compounds was given and there is no evidence that any such compounds have ever been prepared or characterized. The difficulties of preparation of such compounds by conventional routes is discussed in the Siddall and Davis publication. A solution of this problem is the novel synthetic method disclosed herein and in earlier filed application Ser. No. 239,731 filed Mar. 2, 1981.

The novel compounds of the present invention are useful as solvent extraction reagents for the removal or segregation of radionuclides from nuclear fuel or weapons process streams. Compounds of formula 1 were first reported by Zabusova, et al., *Tr. Kazansk. Khim. Technol. Inst.*, (33), 167 (1964). Prepared were compounds of formula 1 where: $R^1 = R^2 = C_2H_5$, $R^3 = R^4 = H$ and $R^5$ and $R^6$ were as follows:

| $R^5$ | $R^6$ |
|---|---|
| H | H |
| $C_2H_5$ | $C_2H_5$ |
| $C_6H_5$ | $C_6H_5$ |
| H | $C_4H_9$ |
| H | $C_6H_5CH_2$ |
| H | $C_6H_5$ |
| H | $p$-$CH_3C_6H_5$ |

In subsequent publications (A. I. Razumov, et al., 5 ibid., 40(2), 212 (1969); A. I. Razumov, *J. Gen. Chem. USSR (Engl. Transl.)*, 39(2), 235 (1969); A. I. Razumov, *Khim. Primen. Fasforerg. Soedin, Tr. Konf.* 4th 1969, 96 (1972) these authors screened these compounds for biological activity and examined them by spectroscopy. No mention is made of utility as solvent extractants for radionuclides and the compounds disclosed in those publications are not known to be useful for solvent extraction.

The July 13, 1981 *Chemical and Engineering News* (at page 51) notes that at the National A.C.S. Meeting, Industrial and Engineering Section, on Aug. 25, 1981, a paper will be presented on Extraction of Am(III) and Cm(III) from Synthetic High-Level Liquid Wastes Using Hexylphenyl-N,N-Diethylcarbamoylmethylphosphine Oxide and Hexylhexyl-N,N-Diethylcarbamoylmethylphosphonate by E. P. Horwitz, D. G. Kaline, L. Kaplan and G. W. Mason.

SUMMARY OF THE INVENTION

The invention involves a process for preparing an organophosphorus compound of the formula 1:

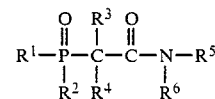

where $R^1$, $R^2$, $R^3$, $R^4$, $R^5$ and $R^6$ are alkyl, aryl or hydrogen, more preferred where $R^1$ and $R^2$ can be different or the same and are selected from alkyl or aryl and $R^3$, $R^4$, $R^5$ and $R^6$ can be different or the same and are selected from hydrogen, alkyl, or aryl, and where at least one of $R^3$ and $R^4$ is preferably hydrogen, and where $R^1$ and $R^2$ and/or $R^5$ and $R^6$ can be in connection forming a heterocyclic ring structure of at least 5 members, said process comprising:

(a) reacting an organophosphorus compound of the formula 2 where $R^1$ and $R^2$ are defined as above:

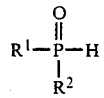

with a 2-substituted alkanoic amide of the formula 3:

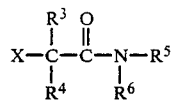

where X is a good leaving group, $R^3$, $R^4$, $R^5$ and $R^6$ are as defined above; and (b) conducting said reaction in a liquid-liquid, two-phase system comprising an aqueous phase containing a high concentration of an aqueous base and an organic phase containing a phase transfer catalyst and under reaction conditions such that degradative hydrolysis of the products or reactants is substantially avoided and such that said organophosphorus compound or formula 1 is a product of said reaction.

The invention novel compounds of the following formula 1 A:

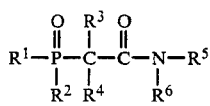

where $R^1$ and $R^2$ can be the same or different and are selected from alkyl groups which together contain a sufficient number of carbon atoms to impart the desired degree of hydrophobicity to the compound. It is preferred that $R^1$ and $R^2$ together contain at least 8 carbon atoms, and particularly preferred that each of $R^1$ and $R^2$ are primary alkyl groups containing at least four carbon atoms. To provide sufficient hydrophobicity, $R^1$ and $R^2$ can be in connection forming a heterocyclic ring structure of about 5 to about 7 members including the phosphorus atom. While not essential, it is preferred that the members of the heterocyclic ring other than the phosphorus atom be carbon atoms, e.g., —(CH$_2$)$_4$—, because such compounds are the simplest to manufacture. $R^3$ and $R^4$ are preferably both hydrogen but one may be hydrogen and the other an alkyl group containing from 1 to 18 carbon atoms or an alkylaryl group such as benzyl or the like. $R^5$ and $R^6$ can be the same or different and are selected from alkyl groups of 1 to 12 carbon atoms, preferably from 1 to 6 carbon atoms. $R^5$ and $R^6$ can be in connection to form a heterocyclic ring structure of about 5 to about 7 members including the amide nitrogen atom, wherein the members of the heterocyclic ring other than the amide nitrogen are preferably carbon atoms, e.g., —(CH$_2$)$_4$—.

Those compounds which are soluble in liquid hydrocarbons, carbons, such as kerosene, white oil, lube oils, octane, diethylbenzene, etc., have a unique utility as solvent extraction reagents for removal and segregation of radionuclides from nuclear fuel and weapon manufacture reprocess streams. These compounds offer superior extraction strength and hydrolytic and radiolytic stability to the known dialkyl N,N-dialkylcarbamoyl-methylphosphonates (CMP's) of the prior art (see U.S. Pat. No. 4,396,556, issued Aug. 2, 1983).

The invention especially involves dialkyl(N,N-dialkylcarbamoylmethyl) phosphine oxides (CMPO's) and processes for their preparation. In addition, some of the CMPO's are crystalline solids, a feature which significantly eases their purification relative to the prior art CMP's which are high-boiling oils. For example, the compound of formula 1, where $R^1=R^2=$n-octyl, $R^3=R^4=$hydrogen, and $R^5=R^6=$methyl, i.e., N,N-dimethylcarbamoylmethyldi(n-octyl)-phosphine oxide, is crystalline, melting at 38.5–40.5° C. The CMPO's which are crystalline can be recrystallized from hydrocarbon solvents to obtain pure products. The compounds are represented by the general formula 1B:

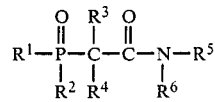

where $R^1$ and $R^2$ are alkyl groups and $R^3$ and $R^4$ are alkyl or aryl groups or hydrogen. Especially preferred are such compounds where:

$R^1$, $R^2$ are the same or different and are alkyl groups together comprising at least 8 carbon atoms, each preferably comprising from 4 to 12 carbon atoms or where $R^1$ and $R^2$ form a heterocyclic ring of about 5 to about 7 members including the phosphorus atom;

$R^3$, $R^4$ are hydrogen or only one of $R^3$ or $R^4$ is an alkyl group of about 1 to about 18 carbon atoms or an alkylaryl group; and $R^5$, $R^6$ are the same or different and are alkyl groups of from 1 to 12 carbon atoms and preferably from 1 to 6 carbon atoms or are in connection to form a heterocyclic ring comprised of about 5 to about 7 members including the amide nitrogen atom.

An especially preferred process for making these compounds follows:

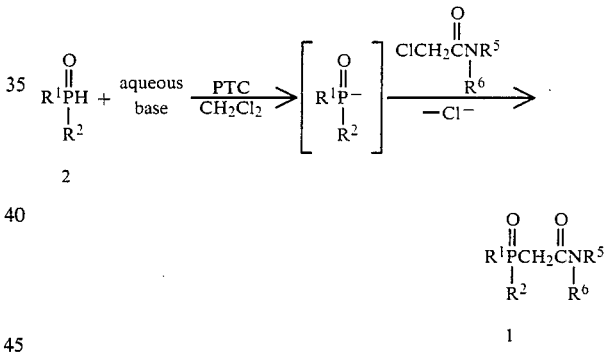

where PTC is a phase transfer catalyst, such as quaternary ammonium compounds and quaternary phosphonium compounds.

Preferably, the phase transfer catalyst is selected from quaternary ammonium compounds and quaternary phosphonium compounds, more preferred from compounds of the formula $Z^1Z^2Z^3Z^4NX'$ or $Z^1Z^2Z^3Z^4PX'$ where $Z^1$, $Z^2$, $Z^3$, $Z^4$ can be the same or different and are selected from alkyl groups containing 1–18 carbon atoms. Preferably no more than one Z group has fewer than 4 carbon atoms and $X'$ is a counterion selected from chloride, perchlorate, hydrogen sulfate, bromide, and hydroxide. For example, one Z group can be an alkyl group containing less than 4 carbon atoms and the other three Z groups can be alkyl groups, which can be the same or different, containing at least 4 carbon atoms. For example, said catalyst can be selected from methyltricaprylammonium chloride, tetrabutylammonium chloride, tetrabutylammonium hydrogen sulfate, tetrahexylammonium chloride, tetrabutylphosphonium chloride, and tetrabutylammonium hydroxide.

Leaving groups are described, for example, in J. March *Advanced Organic Chemistry, Reactions, Mechanisms, and Structure*, pp. 290-94, McGraw Hill, N.Y. (1968). Usually, the best leaving groups are the weakest bases (in nucleophilic displacement reactions). The leaving group should be chosen such that it does not poison the catalyst (as disclosed in greater detail hereinafter and in U.S. Pat. No. 4,396,356).

In the above formula 1 there is virtually no upper limit to the size of $R^1$ and $R^2$ (they can even represent polymer chains of high molecular weight), however, it is preferred that $R^1$ and $R^2$ be selected from: (1) alkyl groups having a combined number of carbon atoms of at least 8, preferably each being a primary alkyl group of from about 4 to about 12 carbon atoms (which can be linear or branched); and (2) less preferred, from any aryl group that does not impart excessive water solubility to compounds of formula II. Preferably, both $R^1$ and $R^2$ are not aryl.

In contrast, if $R^3$ and $R^4$ are of excessive size a detrimental effect upon the reactivity of compounds of formula 3 is observed. Preferably, at least one of $R^3$ and $R^4$ is hydrogen with the other group being selected from hydrogen and primary alkyl groups of about 1 to about 18 carbon atoms (which can be linear or branched) and alkylaryl groups such as benzyl and the like, as long as the group does not impart excessive water solubility to compounds of formula 3.

One of $R^5$ and $R^6$ can be hydrogen, but preferably not both. $R^5$ and $R^6$ are preferably selected from alkyl groups, preferably containing from about 1 to about 12 carbon atoms, more preferably from 1 to 6 carbon atoms (which can be branched or linear) or can form a heterocyclic ring, preferably containing from about 5 to about 7 members including the amide nitrogen atom.

For example, the 2-substituted alkanoic amide can comprise an N,N-dialkylchloroacetamide of the formula:

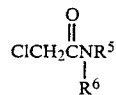

where $R^5$ and $R^6$ are the same or different and are alkyl groups of about 1 to about 12 carbon atoms or can form a heterocyclic ring preferably containing from about 5 to about 7 members including the amide nitrogen atom.

The process is useful for preparing N,N-dimethyl carbamoylmethyl(di-n-octyl)phosphine oxide (that is structure 1, where $R^1=R^2=$n-octyl, $R^3=R^4=$hydrogen, and $R^5=R^6=$methyl) of the formula 1C:

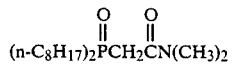

by reacting di(n-octyl)phosphine oxide 2a, that is, the formula 2, where $R^1=R^2=$n-octyl, with N,N-dimethylchloroacetamide 3a, that is, formula 3, where X=Cl, $R^3=R^4=$hydrogen, and $R^5=R^6=$methyl.

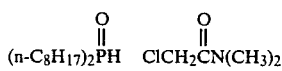

wherein the reaction is conducted at a temperature in the range of about 10° C. to about 60° C. (more preferred about 25° C. to about 45° C.) in a liquid-liquid two-phase system comprising an organic solvent, preferably methylene chloride and an aqueous solution containing about 20 to about 50 weight percent of a strong base, preferably sodium hydroxide the reaction being continued for sufficient time for the compound of formula 3a to substantially completely react with the compound of formula 2a (a stoichiometric excess of either compound can be present) to produce a reaction mixture containing the organophosphorus compound of formula 2a and for insufficient time for the chloroacetamide of formula 3a or the product of formula 1a to be degraded, as by hydrolysis; and, recovering the organophosphorus compound of formula 1a from the reaction mixture.

The base does not react with the chloroacetamide. This enables one to conduct the deprotonation of the dialkylphosphine oxide in the presence of the chloroacetamide. The intermediate conjugate base $[R^1R^2P(O)^-]$, is consumed as formed and never achieves high concentration. Thus, side reactions of this reactive nucleophile are avoided. Additionally the precipitation due to insolubility of alkali metal salts of this conjugate base (see Siddall ibid.) is avoided since only low concentrations are ever present, and they are present as the solubilized quaternary ammonium or phosphonium salt.

According to the invention, novel organic tertiary phosphine oxides such as carbamoylmethylphosphine oxides of formula 1 can be prepared by a process involving phase transfer catalysis, under conditions where degradative hydrolysis of the products and reactants is substantially avoided. For example, novel tertiary carbamoylmethylphosphine oxides can be prepared by reaction of the corresponding secondary phosphine oxides with 2-substituted acetamides (wherever the 2-substitutent is a good leaving group that doesn't "poison" the phase transfer catalyst, e.g., chlorine) in a two-phase system containing a high concentration of an aqueous base (preferably sodium hydroxide) and a suitable phase transfer catalyst, e.g., tetraalkylammonium chlorides. The novel tertiary carbamoylmethylphosphine oxides are useful as extractants for transplutonium elements and for recovering uranium from phosphoric acid.

Carbamoylmethylphosphonates (CMP's) and carbamoylmethylphosphine oxides (CMPO's) can be used for uranium isotope enrichment, to produce fuel enriched in $U^{235}$ for nuclear reactors for power generation.

These materials (CMP's and CMPO's) are specific for complexation of trivalent actinides and they can be used

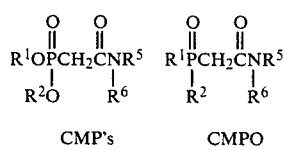

CMP's      CMPO as extractants in a solvent extraction (or liquid ion-exchange) for extracting, preferentially, $U^{238}$ (III) into an organic phase, leaving U(IV) in the aqueous phase enriched in $U^{235}$ (IV). Such extractions can be conducted in aqueous phosphoric acid medium and can be done in conjunction with cycles of oxidation and reduction, for example, oxidation, extraction, reduction then further oxidation, with a stripping step either before or after the reduction. Such extractions can use the techniques described in *Entropie*, No. 78, Nov.–Dec. 1977 by D. Gourisse and J. Guais, in *Nippon Genshiryoka Gakkaishe*, Vol. 20, No. 8 (1978) pp 547–552 and in U.S. 4,274,956 of Stewart.

FURTHER DESCRIPTION

Agitation of two-phase system comprised of an aqueous base, such as sodium hydroxide solution and an organic phase preferably made up of a solvent (although the solvent can be omitted), such as methylene chloride, the reactants, a dialkylphosphine oxide and an N,N-dialkylchloroacetamide, and a catalytic amount of a quaternary ammonium chloride, $(Z)_4NCl$, where $(Z)_4$ represents $Z^1$, $Z^2$, $Z^3$ and $Z^4$ collectively, enables ion exchange between $(Z)_4NCl$ and the sodium hydroxide to occur at the phase interface with distribution of the resultant base, $(Z)_4NOH$, to the organic phase (Eq. 1). There, it is a sufficiently strong base to deprotonate the dialkylphosphine oxide (Eq. 2).

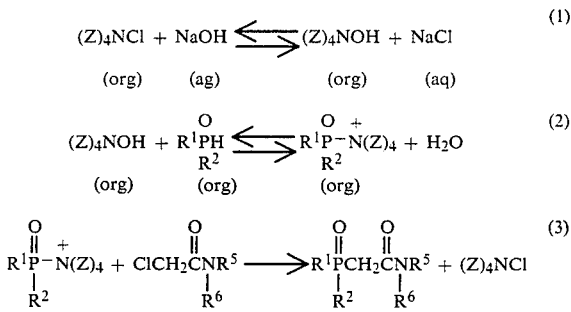

The nucleophilic conjugate base $[R^1R^2P(O)^-]$ reacts as it is formed with the N,N-dialkylchloroacetamide to form the product CMPO directly (Eq. 3). The avoidance of high concentrations of this anion $[R^1R^2P(O)^-]$ is likely the reason (along with the mild conditions) that side products typical of conventional Michaelis-Becker reactions are substantially excluded by this technique. The non-reactivity of the base (aqueous sodium hydroxide) with the chloroacetamide enables this. Precipitation of alkali metal salts of the conjugate base (prior art—Siddall ref.) is avoided.

Hydrophobic aliphatic quaternary ammonium chlorides are the catalysts preferred for favorable organic phase distribution of $(Z)_4NOH$, necessary for effective hydroxide transfer. Additionally, such hydrophobic character of the catalyst enhances organic phase distribution and solubility of the intermediate anion $[R^1R^2P(O)^-]$, facilitating the reaction. The structural features of the catalysts which are conducive to PTC (i.e., phase transfer catalysis) activity in general are those preferred in the process herein described. Phase transfer catalysis has been described, for example, by W. P. Weber and G. W. Gokel, *Phase Transfer Catalysis in Organic Synthesis*, Springer-Verlag, New York (1977), and by C. M. Starks and C. Liotta, *Phase Transfer Catalysis: Principles and Techniques*, Academic Press, New York (1978).

The preferred catalysts are transfer agents for anions, e.g., hydroxide ions, Typical catalysts include quaternary ammonium compounds of the formula $(Z)_4N^+X^-$, (for example: tetrabutylammonium hydrogen sulfate, methyltricaprylylammonium chloride) and quaternary phosphphonium compounds of the formula $(Z)_4P^+X^-$, where Z and X' are defined as above (for example, tetrabutylphosphonium hydroxide or chloride, hexadecyltributylphosphonium bromide or chloride). For further examples, including arsoniums, crown ethers, etc., see Weber and Gokel (Ibid.) and Starks and Liotta (Ibid.).

In the above catalyst formulae, Z can be the same or different, but it is preferred that no more than one Z group have less than 4 carbon atoms. If, for example, one Z group is large (say 16 carbon atoms) and the other three small (1 carbon atom), the compound can have undesirable surface activity (e.g., a cationic surfactant) and can cause emulsion problems and/or facilitate undesirable hydrolysis. In practice, preferred catalysts include methyl tricaprylylammonium chloride (Aliquat 336 of General Mills Chem., or Adogen 464 of Ashland Chem.), tetrabutylammonium hydrogen sulfate, tetrabutylammonium chloride, tetrahexylammonium chloride, tetrabutylphosphonium chloride, tetrabutylammonium hydroxide, etc.

The catalysts can be immobilized on a polymer matrix, as in an ion-exchange resin, so that a triphase catalyst system is employed, see for example, S. L. Regen, *Agnew. Chem. Int. Ed. Engl.* 18, 421 (1979).

In the above catalyst formulae, $X^-$ can be any anion, but should prefer the aqueous phase and should not associate too strongly with the quaternary ion, $(Z)_4N^+$. Examples of the more preferred counterions (i.e., anions) include $Cl^-$ (chloride), $ClO_4^-$ (perchlorate), and $HSO_4^-$ (hydrogen sulfate).

Examples of others that can be useful include $Br^-$ $Y'SO_3^-$, preferably where Y is an alkyl or (bromide), $Y'SO_3^-$, preferably where Y is an alkyl or alkoxyl group of one to four carbon atoms.

If the counterion $(X)^-$ associates with the quaternary ion in large preference to hydroxide, the catalyst is unavailable for $OH^-$ transfer, and thus is "poisoned."

Similarly, the anion generated by the displacement (i.e., the leaving group) should not "poison" the catalyst (see catalyst counterion selection preferences).

The leaving ability and degree of association with quaternary ions of halide leaving groups is:

| | |
|---|---|
| $Cl^- < Br^- < I^-$ | (leaving ability) |
| $Cl^- < Br^- < I^-$ | (degree of association with quaternary) |

Degree of association of the leaving groups with the quaternary ion is more important than its leaving ability; therefore $Cl^-$ is most preferred, bromide is also but less preferred and $I^-$ is not preferred because of possible catalyst "poisoning". Typical useful leaving groups are those described in J. March, *Advanced Organic Chemistry, Reactions, Mechanisms, and Structure*, pp. 290–94, McGraw Hill, N.Y. (1968).

Chloride is preferred for both the catalyst counterion and for the leaving group of the compounds of formula 2. It exchanges readily with other anions such, as hydroxide ion and leads to a favorable equilibrium constant for equation 4. Less preferred anions such as $I^-$, or $Y'SO_3^-$ where Y' is an alkyl or alkoxyl group of greater than 4 carbon atoms and (to a less extent $Br^-$), can associate strongly with $(Z)_4N^+$ in the organic phase (Starks and Liotta, Ibid., P. 67) and diminish its ability to transfer hydroxide ion, so catalyst "poisoning" can result from the presence of such anions.

If the catalyst, (Z)₄NCl, is replaced by a tertiary amine such as tri(n-butyl)amine, no reaction is observed Tertiary amines do not catalyze the desired reaction.

Removal of the catalyst from the product can be accomplished by known techniques (e.g., see Starks and Liotta, page 55, and L. Rafecas and J. J. Artus, *Tetrahedron Lett.*, 21, 977 (1980)). Alternatively, the quaternary ammonium chloride used can be immobilized on an insoluble polymer matrix to form a solid-liquid-liquid triphase catalysis system in which the solid catalyst is easily removed by filtration (S. L. Regen, *Agnew. Chem. Int. Ed. Engl.*, 18, 421 (1979)).

When a conventional laboratory mechanical paddle stirrer is used, the rate of reaction is proportional to the rate of stirring below about 200 rpm, due likely to a mass transfer effect. Above this point, however, the rate of reaction is independent of stirring rate, a common feature of PTC reactions. The rates of potential side reactions involving hydrolysis of the carboxamides, however continue to increase rapidly with increased agitation, so it is advantageous to maintain the stirring speed near 200 rpm to minimize hydrolysis relative to the desired displacement reaction. The optimum degree of agitation is a function of the reactor combination, agitation method and reaction conditions and should be determined experimentally for any given case.

High aqueous phase salt concentrations favor hydroxide transfer (Eq. 4) and reduce aqueous phase distribution of all the organic species, reducing the tendency toward hydrolysis. This also reduces the amount of water available for hydration of the organic ions in the organic phase. Preferably, the ionic strength of the aqueous phase should be at least as great as that of a 20% by weight solution of sodium hydroxide in water. Commercial 50% sodium hydroxide is a more preferred aqueous phase. Other useful salts include mixtures of sodium hydroxide and sodium chloride or sodium sulfate. The primary consideration is to pick a salt whose anion does not poison the catalyst, but which increases the ionic strength of the aqueous phase and provides hydroxide ion for transfer to the organic phase.

Although the use of an organic solvent is not necessary (i.e., bulk phase reaction), best results have been obtained with the use of chlorinated hydrocarbon solvents. These appear to facilitate hydroxide transfer, diminish organic ion hydration in the organic phase, and provide favorable distribution coefficients for the organic species involved. Other useful solvents are described in the books by Weber and Gokel and by Starks and Liotta (Ibid.).

Hydrophobic R groups naturally improve the organic distribution of compounds of formula 2, of its conjugate base, $[R^1R^2P(O)^-]$, and of the product, of formula 1. This feature makes this technique ideally suited for the preparation of solvent extraction reagents for which such hydrophobicity is desirable.

The present invention provides a route to novel tertiary carbamoylmethylphosphine oxides (CMPO's) of formula 1B, which are expected to be stronger extractants than the products of the prior art, i.e., dialkyl N,N-dialkylcarbamoylmethylphosphonates (CMP's) in addition to

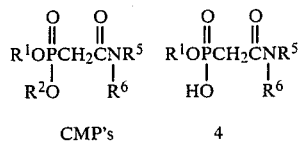

CMP's     4 being more stable to hydrolytic, radiolytic, and thermal conditions. In a reagent for use in solvent extraction, the presence of hydrolysis products of CMP's such as the compound of formula 4 causes serious problems (see Schultz and McIsaac, *Proc. Int. Solvent Extr. Conf.* 1977, *CIM Spec.*, Vol. 21, 619 (1979), and S. Katz and W. D. Bond, *J. Inorg. Nucl. Chem.*, 41, 1781 (1979)). The very high extractant strength of compounds of formula 4 interferes with proper selective stripping. These hydrolyzed products are present in products of the prior art (CMP's) prepared by conventional routes and can result from thermal or radiolytic decay during operation. Such detrimental impurities do not occur by degradation of the novel compounds of this invention. The tertiary phosphine oxide function is not vulnerable to hydrolysis.

Sodium salts of dialkylphosphine oxides are known to be very insoluble, a problem which generally precludes the use of the Michaelis-Becker reaction for the synthesis of trialkylphosphine oxides because the conventional technique involves stoichiometric formation of the salts (see T. H Siddall III and M. H. Davis, *J. Chem. Eng. Data*, 10, 303 (1965)). However, no difficulties with precipitation are encountered during the PTC reaction, suggesting that the quaternary ammonium salts have sufficient solubility at the catalytic concentrations generated in the course of the reaction.

The above procedure was repeated using various starting materials, catalysts, proportions and reaction conditions as shown in Table I. The products of these runs are reported in Table I and are characterized in Table II. These Tables also report, for comparative purposes, results of Examples I, II, and III.

ILLUSTRATIVE EXAMPLES

In the following examples, a Perkin Elmer Sigma I Gas Chromatograph with a flame-ionization detector was used routinely for reaction monitoring and product analysis. A 6×⅛" stainless steel column packed with 3% SE-30 on Chromsorb Q 80/100 was used with helium carrier. Temperature program and carrier gas flow rates were appropriate for the particular analysis. Carefully fractionated, chromatographically pure dibutyl phthalate was used as an internal standard for the quantitative analyses. Nuclear magnetic resonance (NMR) spectra were obtained from 20% solution in CDCl₃ with a Nicolet NT-200 spectrometer operated at 200.067 MHz for ¹H and at 80.98 MHz for ³¹P. The ¹H spectra of the novel compounds are unambiguous, the CH₂ signal appearing as a sharp doublet (Tables II). The proton decoupled ³¹P spectra consists of a sharp singlet (Table II) affording an excellent method of determining phosphorus-containing impurities. Methyltricaprylylammonium chloride was an 85% active commercial product of Ashland Chemicals (Adogen 464).

N,N-dibutylchloroacetamide and N,N-dimethylchloroacetamide were prepared by the procedure described by W. E. Weaver and W. M. Whaley, *J. Am. Chem. Soc.*, 69, 515 (1947) and were 99.5+% by GLC. N,N-diethylchloroacetamide was obtained form ICN/K&K Life Sciences and was 97.7% by GLC. Di(n-butyl)phosphine oxide was obtained from Organometallics, Inc. and was 90% by GLC. Di(n-octyl) phosphine oxide was obtained from Specialty Organics, Inc. and was chromatographically pure. Di(2-ethylhexyl) N,N-diethylcarbamoylphosphonate (CMP 8822) was prepared by the method described in Ser. No. 239,731, filed March 2, 1981, and was 95% by GLC. All other organics utilized were available from common sources and were of reagent quality. Elemental analyses were performed by Galbraith Labs., Inc., Knoxville, Tenn.

EXAMPLE 1

Preparation of N,N-dimethylcarbamoylmethyldi-(n-octyl) phosphine oxide

Into a 500 ml, three-necked, round-bottom flask equipped with a thermowell, a mechanical stirrer, a condenser and a septum, was placed a solution of 13.4 g (0.11 mole) of N,N-dimethylchloroacetamide, 27.4 g (0.10 mole) of di(n-octyl)phosphine oxide, and 1.0 g of Adogen 464 in 150 ml of methylene chloride along with 100 ml of 50% sodium hydroxide solution. The solution was stirred at 300 rpm under a gentle reflux until GLC analysis of removed aliquots (2 hours) indicated the consumption of the starting materials. The aqueous layer was extracted with 50 ml of pentane and the combined organic layers were washed with three 50 ml portions of water followed by one 50 ml portion of saturated sodium chloride solution. After drying over anhydrous potassium carbonate, and filtering, the filtrate was evaporated in vacuo (80° C.; 2mm Hg) to yield 29.5 g of an amber oil which was 77% pure by GLC. Upon cooling, the oil crystallized. Recrystallization from pentane afforded a colorless hygroscopic solid which was chromatographically pure, Mp 38.5–40.5. Analytical data obtained for this product is summarized in Table I.

EXAMPLE II

Preparation of di(n-butyl)N,N-di(n-butyl)carbamoylmethylphosphine oxide

The reaction was conducted as described in example I with the substitution of 22.6 g (0.11 mole) of N,N-di(n-butyl)chloroacetamide and 18.0 g (0.10 mole) of di(n-butyl)phosphine oxide as starting materials. After a reaction period of 5 hours, workup yielded 34.5 g of an amber oil which was 84% pure by GLC. Flash distillation in a Kugelrohr apparatus ($10^{-3}$ mm Hg) produced a colorless oil which was 91% pure by GLC. Analytical data for this product is summarized in Table I.

EXAMPLE III

Preparation of N,N-diethylcarbamoylmethyldi(n-octyl) phosphine oxide (CMPO8822)

The reaction was conducted as described in Example I with the substitution of 16.5 g (0.11 mole) of N,N-diethylchloroacetamide in the place of the N,N-dimethylchloroacetamide, and the substitution of 1.5 g tetra(n-hexyl)ammonium chloride for the Adogen 464. After a reaction period of four hours, workup yielded 37.9 g of an amber oil which crystallized upon cooling, but remelted at room temperature.

TABLE I

Summary of Analytical Data for Tertiary Carbamoylmethylphosphine Oxides (CMPO's).

| CMPO Product 1 | $\delta^1 HCH_2{}^a$ | $\delta^{31}P^b$ | $J\ ^{31}PCH^c$ | Purity$^d$ | | C(%) | H(%) | N(%) | (P %) |
|---|---|---|---|---|---|---|---|---|---|
| $R^1=R^2=R^5=R^6$=n-$C_4H_9$; $R^3=R^4$=H | 2.96 | 48.27 | 15.1 | 91$^e$ | Calcd | 65.22 | 11.56 | 4.23 | 9.34 |
| | | | | | Found | 66.35 | 11.56 | 4.15 | 8.87 |
| $R^1=R^2$=n-$C_8H_{17}$; $R^3=R^4$=H; $R^5=R^6=CH_3$ | 2.96 | 47.61 | 14.0 | 100$^f$ | Calcd | 66.81 | 11.77 | 3.90 | 8.61 |
| | | | | | Found | 66.94 | 11.64 | 3.87 | 8.71 |
| $R^1=R^2$=n-$C_8H_{17}$; $R^3=R^4$=H; $R^5=R^6=C_2H_5$ | 2.97 | 48.30 | 14.8 | 85$^g$ | Calcd | 68.18 | 11.96 | 3.61 | 7.99 |
| | | | | | Found | 68.00 | 12.01 | 3.53 | 7.98 |

$^a$<sup>1</sup>H NMR chemical shift (ppm) of methylene protons signal (center of observed doublet) relative to tetramethylsilane.
$^b$<sup>31</sup>PNMR chemical shift (ppm) of the phosphorus atom (decoupled) downfield from 85% phosphoric acid.
$^c$<sup>1</sup>H NMR coupling constant (Hz) for the splitting of the methylene protons signal by the $^{31}P$ atom.
$^d$Minimum weight percent obtained by GLC.
$^e$Flash distilled, $10^{-3}$ mm Hg (Kugelrohr apparatus).
$^f$Recrystallized from pentane, mp 38.5–40.5
$^g$Undistilled crude product.

but remelted at room temperature.
GLC analysis indicated a product purity of 85%. Analytical data obtained for this product is summarized in Table I.

EXAMPLE IV

Preparation of Dinonylphenyl Acid Phosphate (DNPAP)

This example shows the synthesis of DNPAP which is useful in illustrating the utility for improving the extraction of uranium of the process described herein.

Into a one liter three-necked, round-bottom flask fitted with a mechanical stirrer, a thermowell, a pressure-equalizing addition funnel, and inert gas fittings was placed 306.7 g (2 moles) of phosphoryl chloride and 100 ml of anhydrous ethyl ether. To the stirred solution, under a nitrogen atmosphere, was added a solution of 173 g (0.5 mole) of dinonylphenol (Productol Chemical Co.), 40.0 g (0.51 mole) of pyridine, and 200 ml of anhydrous ethyl ether at a rate which permitted maintenance of the reaction temperature at 25° C. by means of an ice bath. When the addition was complete, the mixture was filtered by suction to separate the precipitated pyridine hydrochloride. The filtrate was evaporated in vacuo and the residue dissolved in 120 ml of 1,2-dimethoxyethane. The solution was returned to the reaction flask and to it added, with vigorous stirring, 200 ml of deionized water with maintenance of the solution temperature at 25° C. by means of an ice bath. After completion of the addition, the mixture was stirred an additional hour and the phases allowed to separate. The organic layer was washed with 200 ml of fresh water, then evaporated in vacuo to yield 194.5 g (91%) of a clear viscous amber oil.

EXAMPLE V

This example illustrates a laboratory test procedure which can be used to determine the utility of uranium extractants or uranium extractant synergists of any of the products of the process as described herein.

Extraction of Uranium from Wet-Process Phosphoric Acid

Shake tests were performed using "green" wet process phosphoric acid (43% $P_2O_5$) produced in Florida by "OXY Hemihydrate Process" which, after pretreatment with activated charcoal (by the procedure described in B. D. Wells, "Treatment of Wet Process Phosphoric Acid With Activated Carbon", paper presented at the ACS National Meeting, Las Vegas, Nev., August, 1980), contained 40 mg/l uranium. The extractant composition being tested was dissolved in Chevron Alkylate 100 (a mixture of alkylbenzenes) to produce the solution concentrations shown in Table II.

The Florida "black" phosphoric acid was pretreated with "Calgon" activated charcoal at ambient temperature to remove organic impurities and produce a "green" acid.

A portion of the green acid was reduced with iron nails to 110–130 mV (measured with a platinum redox electrode) and another portion was oxidized with chlorate to 1100–1115 mV.

A 1:1 volume ratio mixture was made of a sample of each such reacted (i.e., reduced or oxidized) acid, "green" acid and the extractant solution. The sample mixtures were maintained at 40° C. by means of a temperature bath.

In the following Table II, "DNPAP" is dinonylphenyl acid phosphate; "TOPO" is trioctylphosphine oxide; "CMP 8822" is di(2-ethylhexyl)N,N-diethylcarbamoylmethylphosphonate; "CMPO 8822" is N,N-diethylcarbamoylmethyldi(noctyl)phosphine oxide; and, "DEHPA" is di(2-ethyl)hexylphosphoric acid.

TABLE II

| Run | Extractant (conc) | $K_{U+4}$ | $K_{U+6}$ |
|-----|-------------------|-----------|-----------|
| (a) | DNPAP (0.5 M) | 5.97 | 1.61 |
| (b) | DNPAP (0.5 M) + TOPO (0.125 M) | 7.14 | 1.19 |
| (c) | DNPAP (0.5 M) + CMP 8822 (0.125 M) | 10.4 | 2.02 |
| (d) | DNPAP (0.5 M) + CMPO 8822 (0.125 M) | 21.5 | 1.85 |
| (e) | DEHPA (0.5 M) + TOPO (0.125 M) | 0.01 | 0.60 |

Runs (a) and (b) are used as comparison runs. Runs (b), (c) and (d) show the enhanced uranium extraction due to the presence of the indicated neutral organophosphorus synergist.

Similar tests can be made to determine synergistic effect, by replacing the DNPAP with other acidic organophosphorus extractants; however, with some extractants, little or no synergism may be observed with the neutral organophosphorus compounds of runs (b)(c) and (d).

The novel CMPO's described herein can be used as solvent extraction reagents for removal or segregation of radionuclides from nuclear fuel and weapon manufacture and from reprocess streams, as by the techniques in U.S. Pat. No. 3,993,728 and related known processes.

The novel CMPO's described herein can be useful in a liquid-liquid extraction process for the recovery and partitioning of actinide values selected from the group consisting of Am (III), Cm (III), Pu (IV), Np (IV) and U (VI), from acidic nuclear waste aqueous solutions comprising the steps of contacting said aqueous solutions with an organic phase comprising at least one CMPO to thereby extract said actinide values into the organic phase, contacting said actinide-loaded organic phase with an aqueous dilute (about 0.1 M) nitric acid solution to extract the trivalent actinide values into the aqueous phase, contacting the organic phase containing the tetravalent and hexavalent actinide values with an aqueous solution of about 0.1 M nitric-hydrofluoric acid to thereby extract the tetravalent actinide values into the aqueous phase and thereafter contacting the organic phase containing the hexavalent actinide values with a dilute solution of sodium carbonate to thereby remove the hexavalent actinide values from said organic phase. Especially preferred CMPO's for this process include those of formula 1B, especially where $R^1$ and $R^2$ are octyl or n-hexyl, $R^3$ and $R^4$ are hydrogen and $R^5$ and $R^6$ are selected from methyl ethyl, n-butyl, 2-ethylhexyl, or joined to form a ring.

What is claimed is:

1. Actinide extraction Compounds of the following formula

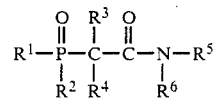

wherein $R^1$ and $R^2$ are the same or different and are selected from primary alkyl groups of 4 to 12 carbon atoms; $R^3$ and $R^4$ are hydrogen or only one of $R^3$ and $R^4$ is hydrogen and the other is selected from alkyl groups of 1 to 18 carbon atoms; and $R^5$ and $R^6$ are the same or different and are selected from primary alkyl groups of 1 to 12 carbon atoms or where one of $R^5$ and $R^6$ is hydrogen and the other is selected from primary alkyl groups of 1 to 12 carbon atoms, or where $R^5$ and $R^6$ are in connection forming a heterocyclic ring structure comprised of about 5 to 7 members including the amide nitrogen atom.

2. The compounds of claim 1 wherein $R^5$ and $R^6$ are selected from alkyl groups having from 1 to 6 carbon atoms.

3. The compounds of claim 1 which are crystalline and melt above about 20° C.

4. The compounds of claim 1 wherein $R^1$ and $R^2$ are the same or different and are selected from alkyl groups of 4 to 12 carbon atoms, $R^3$ and $R^4$ are hydrogen, and $R^5$ and $R^6$ are the same or different and are selected from alkyl groups of 1 to 6 carbon atoms or are in connection to form a heterocyclic ring of 5 to 7 members including the amide nitrogen.

5. The compounds of claim 4 wherein $R^1$ and $R^2$ are n-octyl, $R^3$ and $R^4$ are hydrogen and $R^5$ and $R^6$ are the same and are selected from methyl and ethyl or are in connection as —$(CH_2)_4$—.

6. The compounds of claim 1 wherein $R^1$ and $R^2$ are n-hexyl, $R^3$ and $R^4$ can be the same or different and are selected from hydrogen and methyl, $R^5$ is selected from hydrogen, methyl, and ethyl and $R^6$ is selected from n-butyl, 2-ethylhexyl and ethyl.

7. The compounds of claim 6 wherein $R^5$ and $R^6$ are ethyl.

8. The compounds of claim 6 wherein $R^5$ is methyl and $R^6$ is n-butyl.

9. The compounds of claim 6 wherein $R^5$ is hydrogen and $R^6$ is 2-ethylhexyl.

* * * * *